United States Patent [19]

Hartwell

[11] Patent Number: 4,947,417

[45] Date of Patent: Aug. 7, 1990

[54] ADJUSTING ARRANGEMENT FOR RADIO-DIAGNOSTIC EQUIPMENT

[75] Inventor: Garry Hartwell, Troy, Va.

[73] Assignee: The University of Virginia Alumni Patents Foundation, Charlottesville, Va.

[21] Appl. No.: 285,485

[22] Filed: Dec. 16, 1988

[51] Int. Cl.$^5$ .............................................. G21K 1/02
[52] U.S. Cl. ...................................... 378/147; 378/37; 378/150
[58] Field of Search .................. 328/37, 147, 150–153; 250/505.1

[56] References Cited

U.S. PATENT DOCUMENTS 4,825,455  4/1989  Bauer ...................................... 378/37

FOREIGN PATENT DOCUMENTS 1147069  5/1983  Canada .
0059382  9/1982  European Pat. Off. .
0178728  4/1986  European Pat. Off. .
2083086  12/1971  France .

OTHER PUBLICATIONS

Book entitled "Rontgen-aufnahmetechnik", by Erwin A. Hoxter, 1979, p. 28.

Primary Examiner—Carolyn E. Fields
Assistant Examiner—David P. Porta
Attorney, Agent, or Firm—Lawrence C. Edelman

[57] ABSTRACT

An effective ray beam includes an arc-shaped cut-out element having its open side facing in the direction toward the center of a ray beam. Via a variable arrangement of the arc-shaped cut-out element in a plane perpendicular to the ray beam, the effective ray beam can be individually adjusted to an arc-shaped object under examination.

6 Claims, 2 Drawing Sheets

ADJUSTING ARRANGEMENT FOR RADIO-DIAGNOSTIC EQUIPMENT

BACKGROUND OF THE INVENTION

1. Field of the Invention

The invention relates to radio-diagnostic equipment for radiographic mamma diagnostics having an adjusting arrangement in the ray path of an X-ray tube which has an adjustable element, one side of the adjustable element is positionable in the direction of the effective ray beam for adjusting the effective ray beam emitted by the X-ray tube.

2. Background of the Invention

In known X-ray diagnostic equipment the X-radiation emitted by the X-ray tube is adjusted with adjusting arrangements arranged in the path of the rays of the tube on their way to the object to be examined. The adjusting arrangement consists of plate-shaped elements, which are slidably arranged in a plane perpendicular to the center ray of the X-ray tube, so that the effective ray beam in the region of the object to be examined can be adjusted to a square or rectangular area.

This adjusting arrangement is not suited for superimposing the effective ray beam onto an arc-shaped examination object, such as, for example, a female breast.

It is therefore an object of the invention to design the adjusting arrangement of radio-diagnostic equipment in such manner that the effective ray beam can be adjusted to an arc-shaped examination object.

SUMMARY OF THE INVENTION

In accordance with principles of the invention, the adjustable element has an arc-shaped cut-out extending towards the center of the ray beam so that the effective ray beam is adapted to an arc-shaped examination object.

An advantage of this design is that the effective ray beam can be optimally adapted to an arc-shaped object under examination, in particular in mammography, so that exposure to rays for the person under examination is decreased and ray scattering is reduced.

It is of particular advantage if the adjustable element is essentially cylinder-shaped and rotatably mounted around its longitudinal axis and if the arc-shaped cut-out is positioned unsymmetrically relative to its axis of rotation. This permits the effective ray beam to be individually adjustable to an examination object through rotation of the cylinder-shaped element.

It is also advantageous if the arc-shaped cut-out extends symmetrically with respect to a plane perpendicular to the axis of rotation and in the direction of the center of the effective ray beam. This permits adjusting the effective ray beam symmetrical to its center ray.

In accordance with a further aspect of the invention, the adjustable element is plate-shaped and slidably arranged in a plane perpendicular to the central ray so that the effective ray beam can be individually adjusted to an arc-shaped examination object.

It is also advantageous if the adjusting arrangement is arranged on a side of the housing of the X-ray tube facing the examination object and slidable in a plane perpendicular to the center ray since therewith the effective ray beam can be adjusted to an examination object arranged off center with respect to the central ray.

Other features and advantages of the invention will be apparent from the following description of the preferred embodiments, and from the claims.

For a fuller understanding of the present invention, reference should now be made to the detailed description of the preferred embodiments of the invention and to the accompanying drawings.

DETAILED DESCRIPTION OF THE INVENTION

Figure 1:
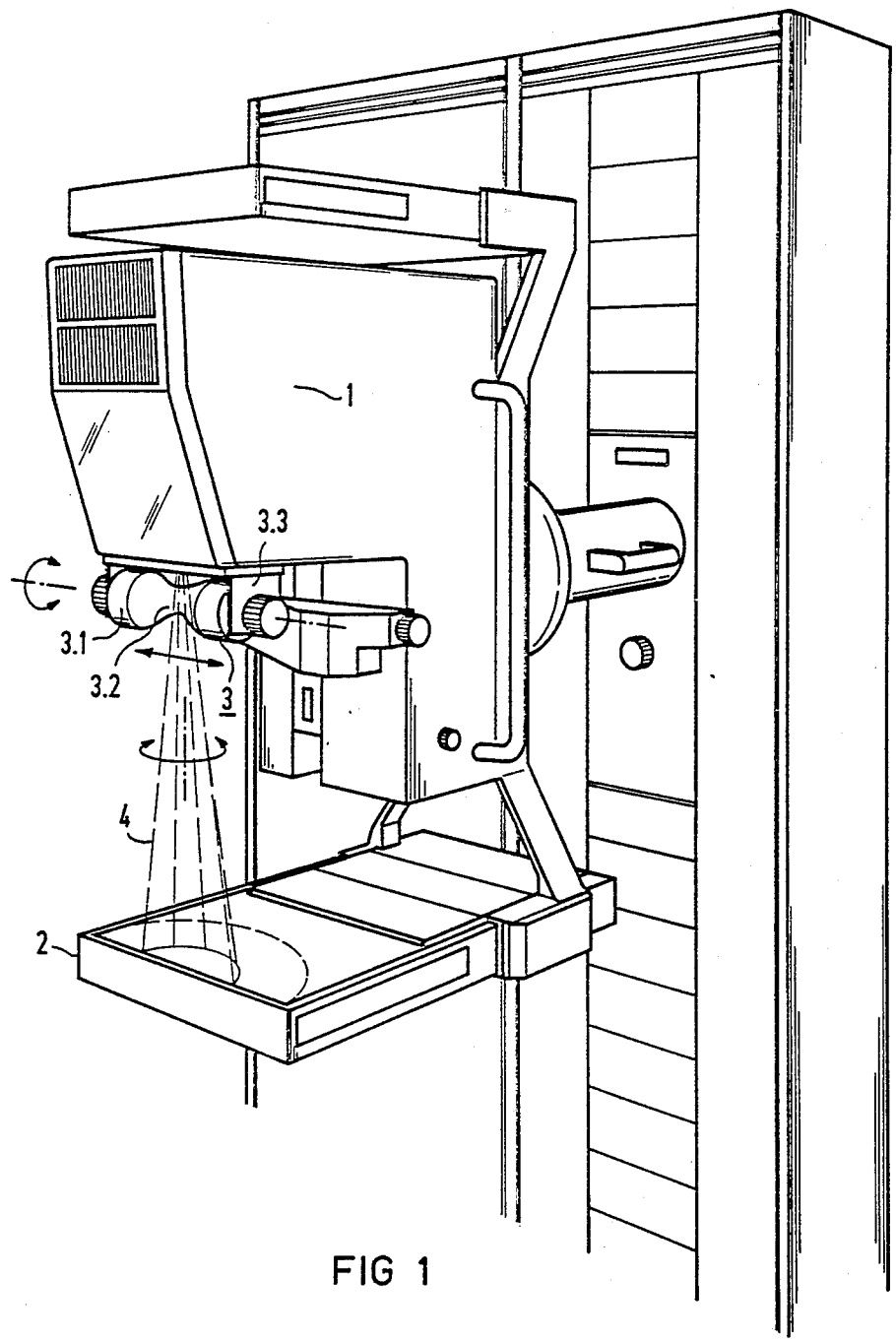
FIG. 1 shows an adjusting arrangement according to the invention having a cylinder-shaped element for the arc-shaped adjustment of the effective ray beam.

FIG. 1 shows an X-ray source 1 having an examination plane 2 arranged perpendicular to the effective ray beam 4 of the X-ray source 1. Arranged on the side of X-ray source 1 facing examination plane 2 is an adjusting arrangement 3 having a cylinder-shaped element 3.1 for adjusting the shape of the effective ray beam 4. Cylinder-shaped element 3.1 has an arc-shaped cut-out 3.2, which, with respect to the longitudinal axis of the cylinder-shaped element 3.1, is positioned unsymmetrically. Cylinder-shaped element 3.1 is mounted rotatably around the longitudinal axis of element 3.1, so that the effective ray beam 4 through rotation of the cylinder-shaped element 3.1 and owing to the arc-shaped cut-out 3.2 can be adjusted to an arc-shaped examination object like the female breast, for example. In the FIG. 1 embodiment cylindrical element 3.1 is additionally mounted so as to be slidable in the direction of the longitudinal axis of element 3.1. This permits symmetrical adjustment of the effective ray beam 4 for examination of an object supported off center on examination plane 2 through displacement of cylinder-shaped element 3.1 in the direction of its longitudinal axis. A corresponding displacement of the entire adjusting arrangement 3 with its mounting support is, of course possible to accomplish the identical result. Additionally, the adjusting arrangement 3 can be mounted rotatably around the center ray of ray beam 4 or around a parallel to it, in order to do justice to the particular recording requirements. By arranging cylinder-shaped element 3.1 in the effective ray beam 4, a semi-transparent transition region is obtained, extending from one side which confines the radiation.

Figure 2:
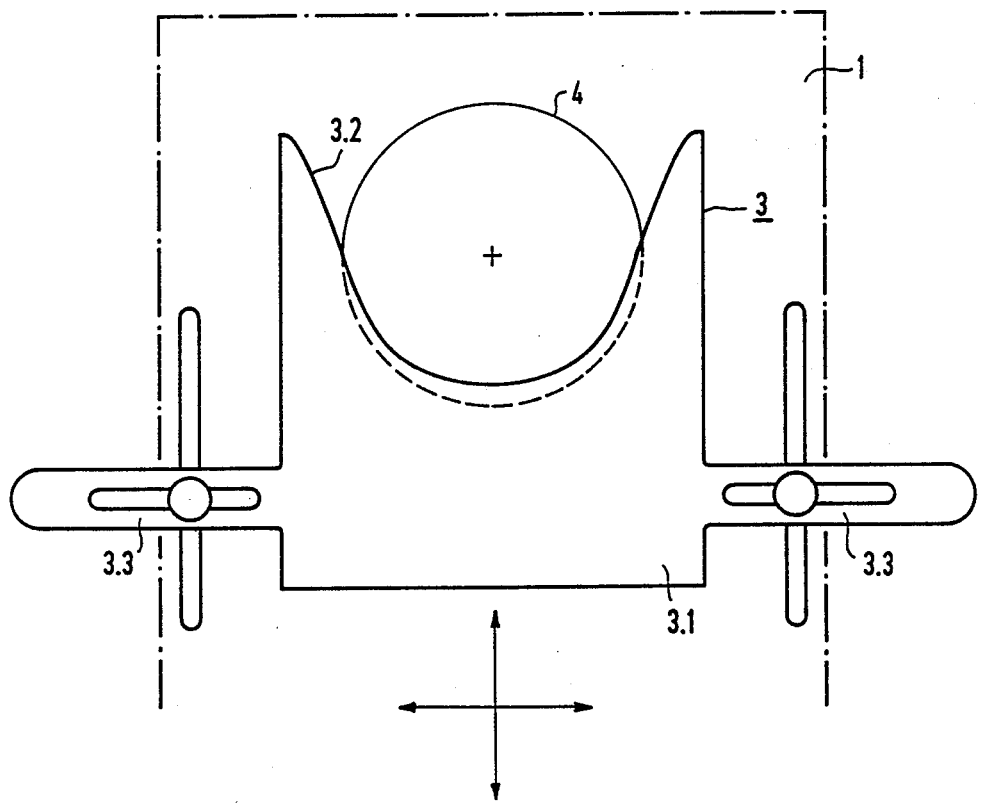
FIG. 2 shows an alternative arrangement according to the invention wherein a plate-shaped element is used for arc-shaped adjustment of the effective ray beam.

The plate-shaped adjustment arrangement shown in FIG. 2 provides a similar functional result as the arrangement shown by FIG. 1. In FIG. 2, plate-shaped element 3.1 is slidably mounted by means of fastening elements 3.3 on the side of X-ray source 1 facing the examination object. Plate-shaped element 3.1 has on the side facing effective ray beam 4 of X-ray source 1 an arc-shaped cut-out 3.2. By displacing the plate-shaped element 3.1 in the effective ray beam of X-ray source 1, the effective ray beam can be adjusted in an arc shape individually to examination objects supported off center on examination plane 2.

Thus, there has been shown and described novel apparatus for adjusting the effective ray beam of a radio diagnostic equipment which fulfills all the objects and advantages sought therefore. Many changes, modifications, variations and other uses and applications of the subject invention will, however, become apparent to those skilled in the art after considering this specification and the accompanYing drawings which disclose a preferred embodiment thereof. All such changes, modifications, variations and other uses and applications which do not depart from the spirit and scope of the invention are deemed to be covered by the invention which is limited only by the claims which follow.

I claim:

1. Radio diagnostic equipment for radiographic mamma diagnostics having an adjusting arrangement arranged in the ray path of an X-ray source which has an adjustable element, one side of the adjustable element being arranged in a direction towards the effective ray beam for adjusting the effective ray beam emitted by the X-ray source, wherein:

said adjustable element is essentially cylinder-shaped and rotatably supported around its longitudinal axis with an arc-shaped cut-out extending from said one side unsymmetrically with respect to its axis of rotation, so that the effective ray beam is able to be adjusted so as to have an arc-shape which is similar to an arc-shaped examination object.

2. Apparatus according to claim 1, wherein said arc-shaped cut-out extends symmetrically with respect to a plane perpendicular to its axis of rotation and which is in the direction of the center of the effective ray beam.

3. Apparatus according to claim 1, wherein said adjusting arrangement is arranged on the side of the X-ray source housing which faces the examination object and is slidably supported in a plane perpendicular to the center of the ray beam.

4. Apparatus according to claim 1, wherein said cylindrical-shaped element is slidably supported in its axial direction.

5. Apparatus according to claim 1, wherein said adjusting arrangement is rotatably mounted around the center of the ray beam.

6. Apparatus according to claim 1, wherein said adjusting arrangement is rotatably mounted around a parallel to the center of the ray beam.

* * * * *